US009823243B2

(12) United States Patent
Imai et al.

(10) Patent No.: US 9,823,243 B2
(45) Date of Patent: Nov. 21, 2017

(54) IMMUNOANALYSIS METHOD AND IMMUNOANALYSIS DEVICE

(71) Applicant: Hitachi High-Technologies Corporation, Tokyo (JP)

(72) Inventors: Kyoko Imai, Tokyo (JP); Toshiro Saito, Tokyo (JP); Kazumichi Imai, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/418,990

(22) PCT Filed: Jun. 21, 2013

(86) PCT No.: PCT/JP2013/067023
§ 371 (c)(1),
(2) Date: Feb. 2, 2015

(87) PCT Pub. No.: WO2014/021020
PCT Pub. Date: Feb. 6, 2014

(65) Prior Publication Data
US 2015/0212082 A1    Jul. 30, 2015

(30) Foreign Application Priority Data
Aug. 3, 2012  (JP) .................................. 2012-172483

(51) Int. Cl.
*G01N 21/75* (2006.01)
*G01N 33/543* (2006.01)
*G01N 21/64* (2006.01)

(52) U.S. Cl.
CPC ... *G01N 33/54386* (2013.01); *G01N 21/6428* (2013.01); *G01N 21/6452* (2013.01); *G01N 33/54326* (2013.01); *G01N 33/54366* (2013.01)

(58) Field of Classification Search
CPC ......... G01N 33/54326; G01N 35/0098; G01N 27/745; B01L 3/502761; B01L 2400/043
See application file for complete search history.

(56) References Cited

U.S. PATENT DOCUMENTS 4,537,861 A * 8/1985 Elings .................... G01N 21/17
356/317
2004/0005718 A1   1/2004 Fukushima
(Continued)

FOREIGN PATENT DOCUMENTS

JP    2003-279570    10/2003
JP    2004-298018    10/2004
(Continued)

OTHER PUBLICATIONS

Mark Schena et al., Quantitative Monitoring of Gene Expression Patterns with a Complementary DNA Microarray, Science, vol. 270, Oct. 1995, pp. 467-470.
(Continued)

*Primary Examiner* — Dennis M White
(74) *Attorney, Agent, or Firm* — Mattingly & Malur, PC

(57) ABSTRACT

An object of the present invention is to provide a highly sensitive immunoanalysis method and analysis apparatus. The invention relates to an analysis method and an analysis apparatus which are constituted in such a way that a component to be measured is reacted with capture component specifically reacting thereto and the reactant is labeled when the component to be measured is present and which are characterized by analyzing the component to be measured with single-molecule sensitivity and resolution by arranging the labeled reactant in a spatially separated certain position and detecting the label of the labeled reactant.

14 Claims, 8 Drawing Sheets

(56) References Cited

U.S. PATENT DOCUMENTS

| | | | |
|---|---|---|---|
| 2004/0259094 A1 | 12/2004 | Odedra et al. | |
| 2008/0160634 A1* | 7/2008 | Su | G01N 27/745 436/501 |
| 2011/0281320 A1* | 11/2011 | Saito | C12Q 1/6816 435/176 |

FOREIGN PATENT DOCUMENTS

| | | |
|---|---|---|
| JP | 2004-333401 | 11/2004 |
| JP | 2008-249446 | 10/2008 |
| JP | 2010-236945 | 10/2010 |
| JP | 2011-200141 | 10/2011 |
| JP | 2012-058114 | 3/2012 |
| JP | 2012-070654 | 4/2012 |

OTHER PUBLICATIONS

Jordan M. Cummins et al., The Colorectal MicroRNAome, PNAS, Mar. 2006, vol. 103, No. 10, pp. 3687-3692.

David M. Rissin et al., Single-molecule enzyme-linked immunosorbent assay detects serum proteins at subfemtomolar concentrations, Nature Biotechnology, Advance Online Publication, May 2010, pp. 1-6.

* cited by examiner

[FIG. 1]
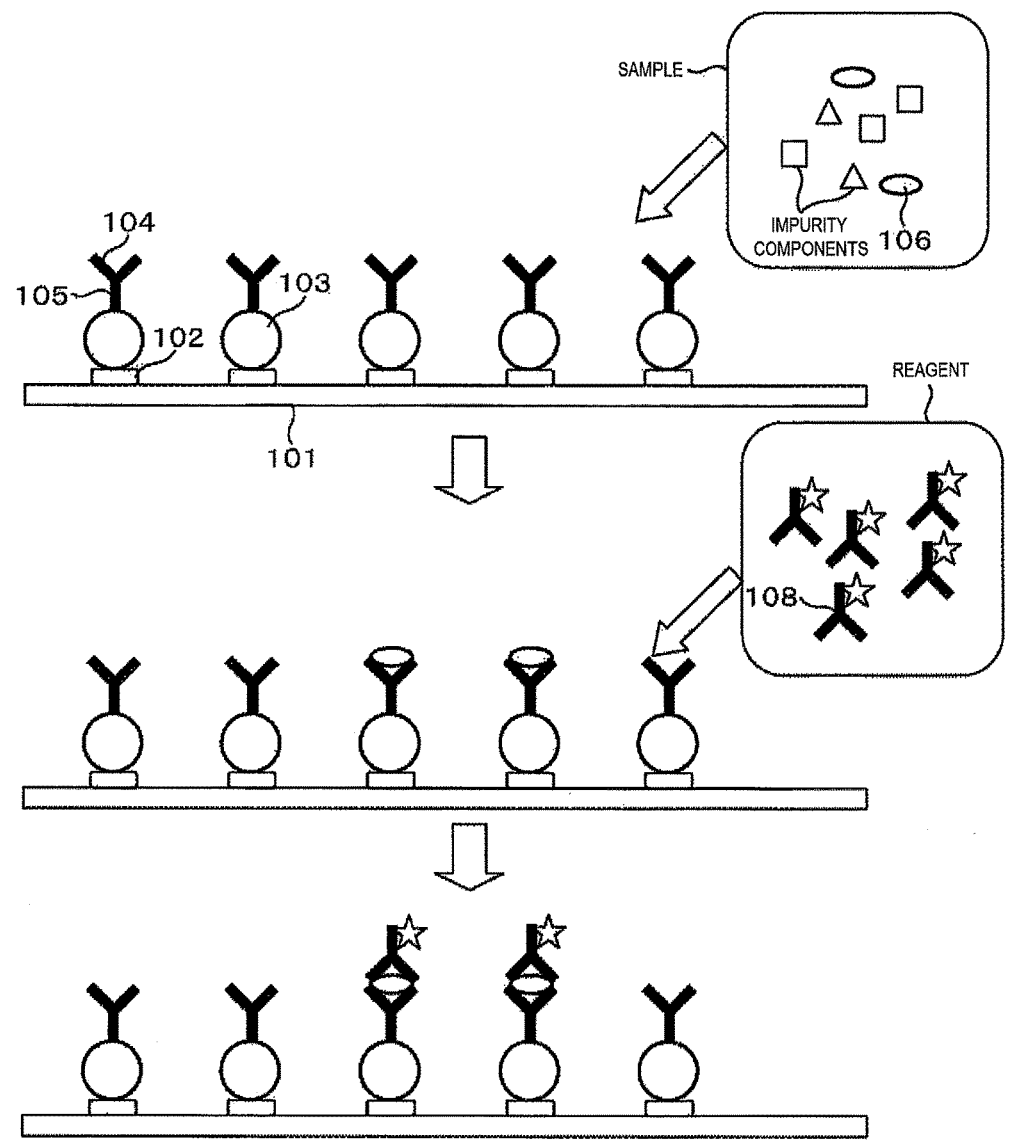

[FIG. 2]
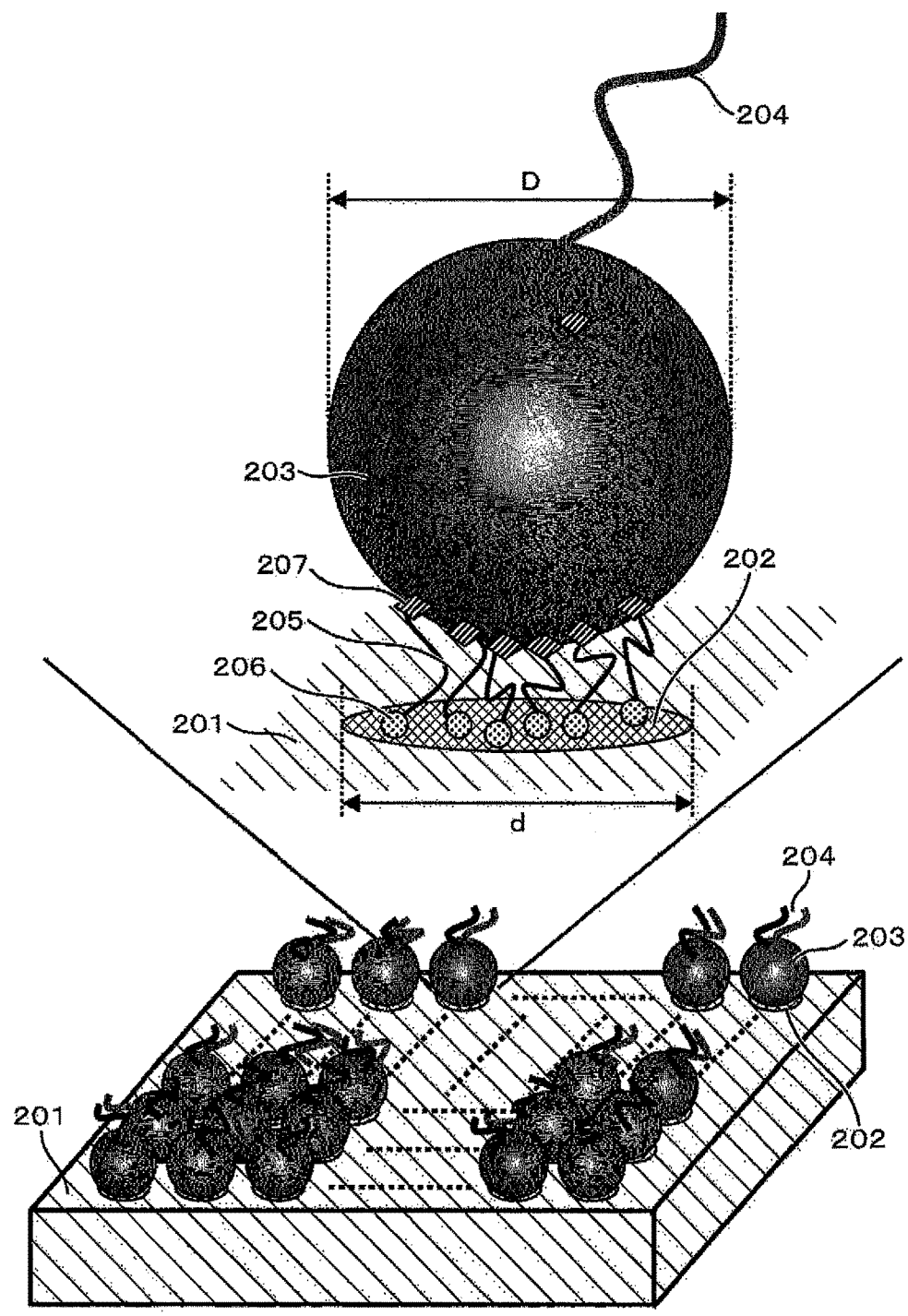

[FIG. 3]
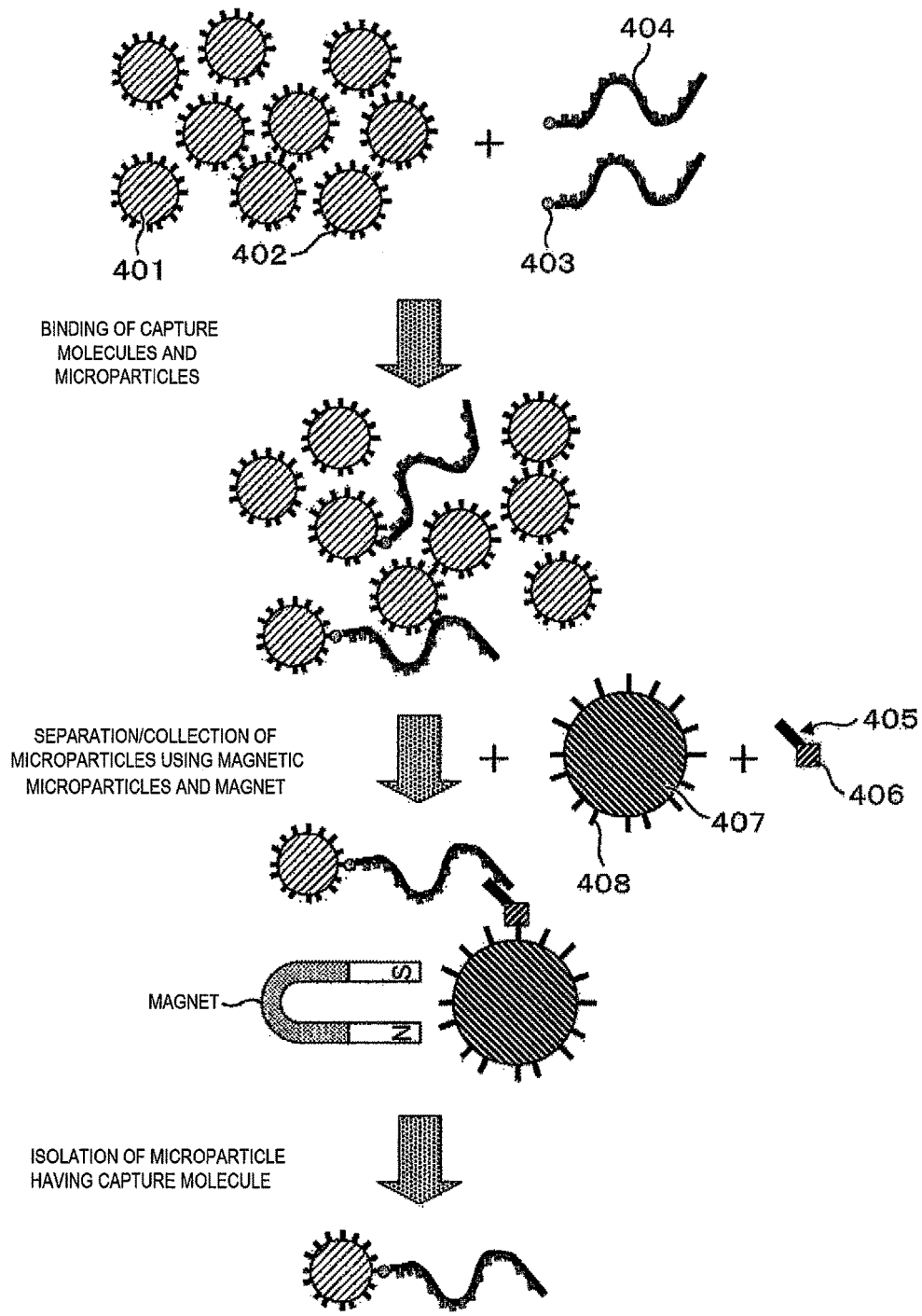

[FIG. 4]
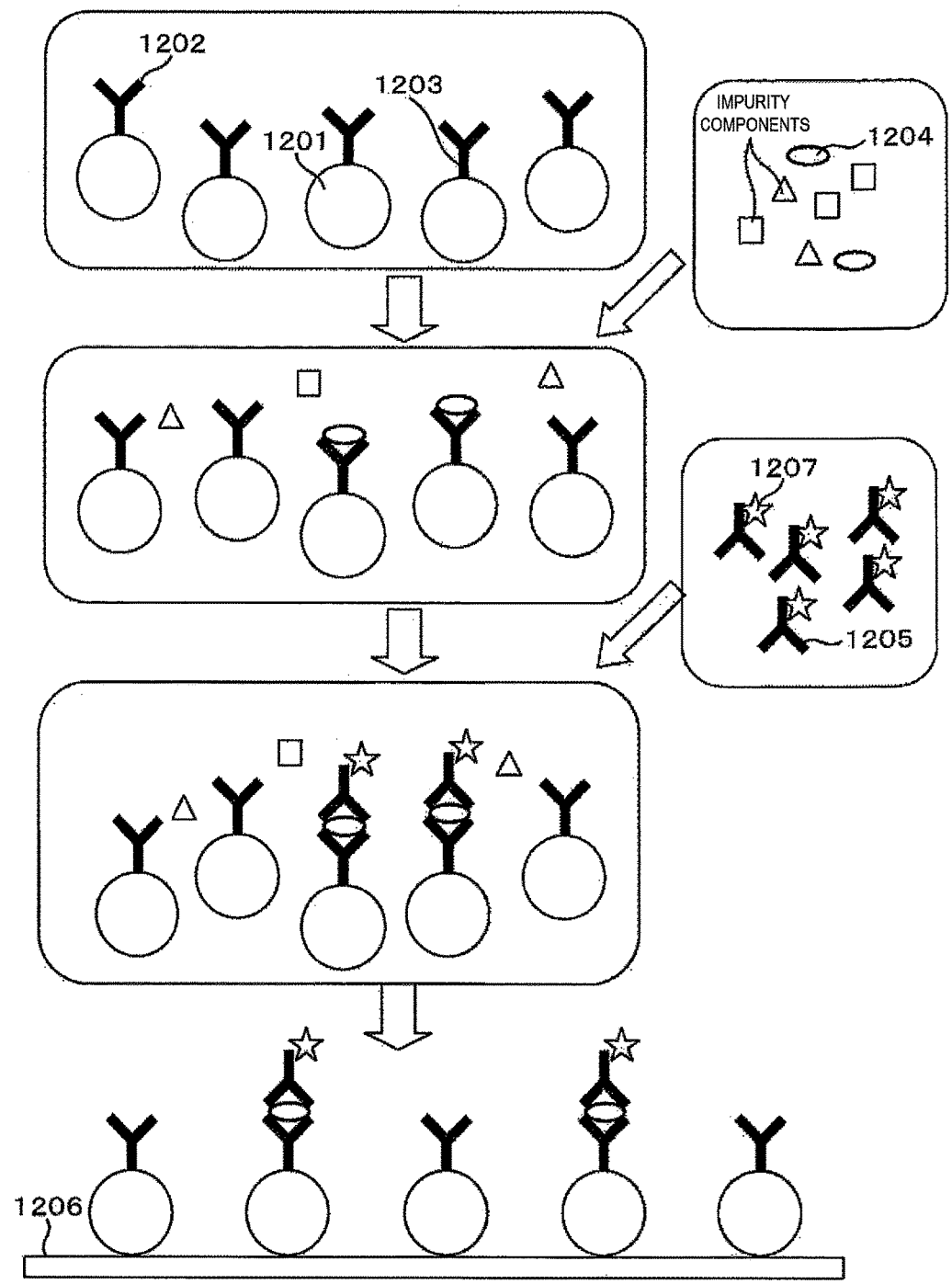

[FIG. 5A]
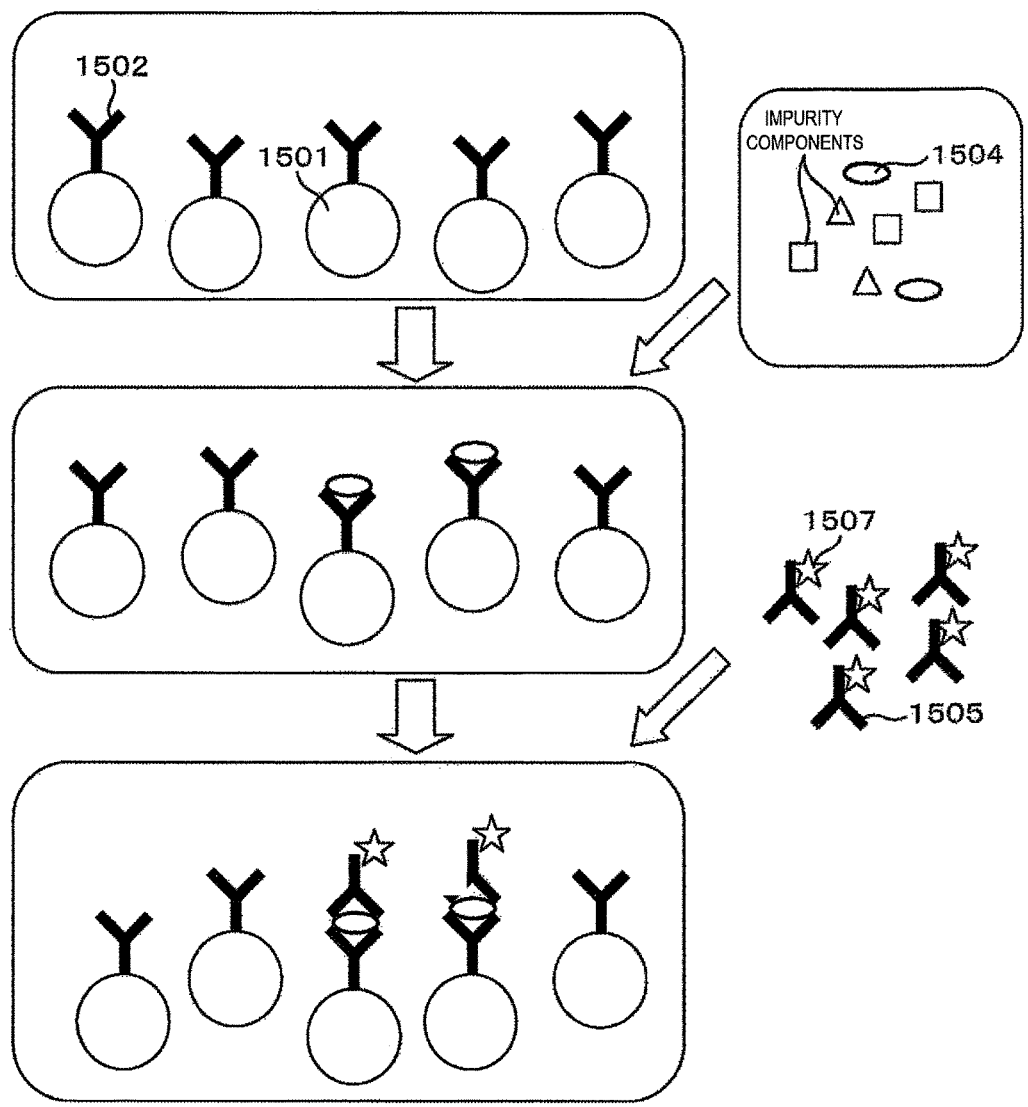

[FIG. 5B]
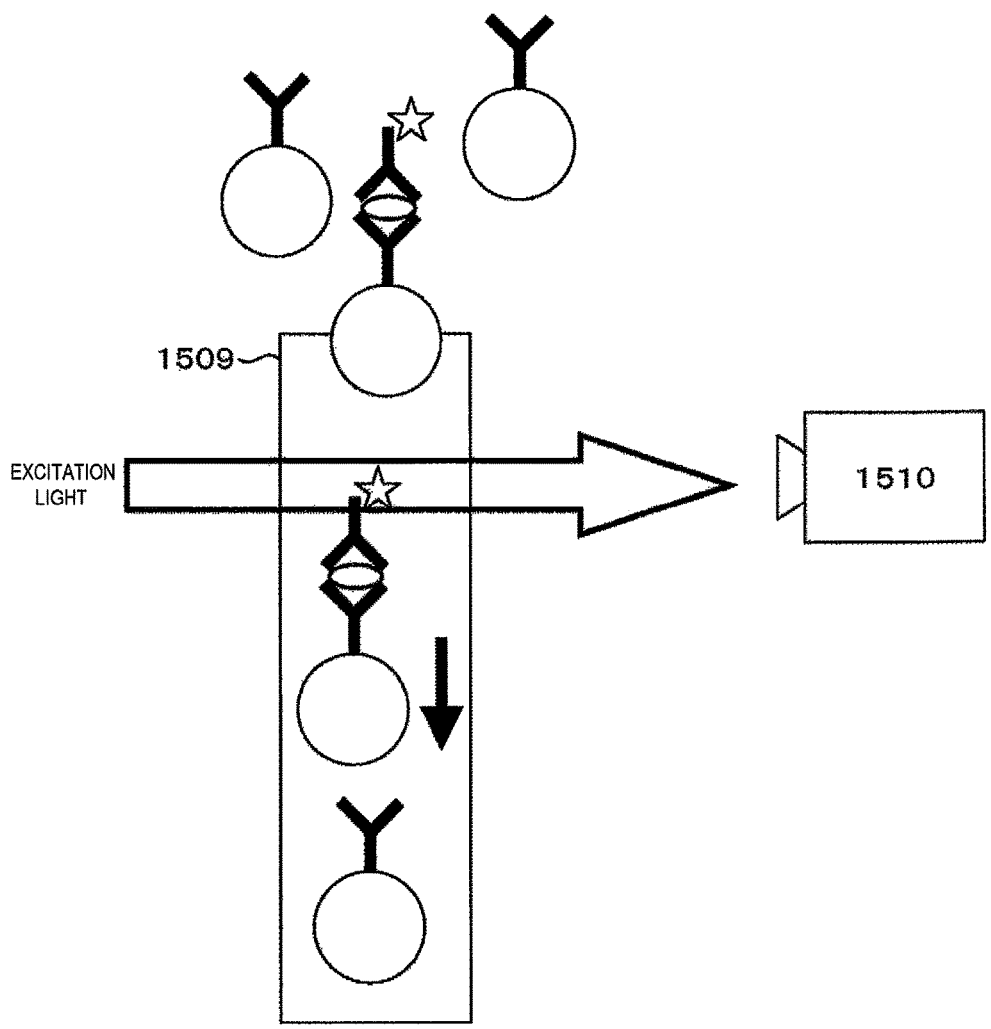

[FIG. 6]
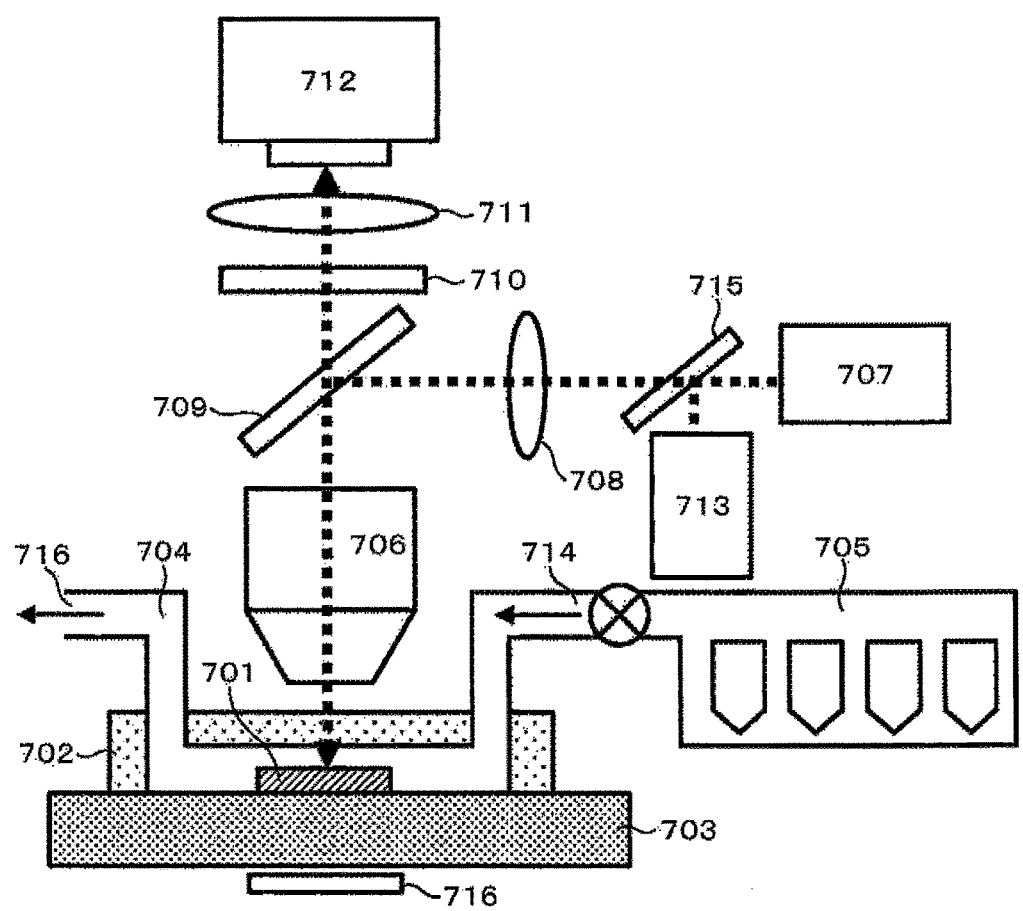

[FIG. 7]
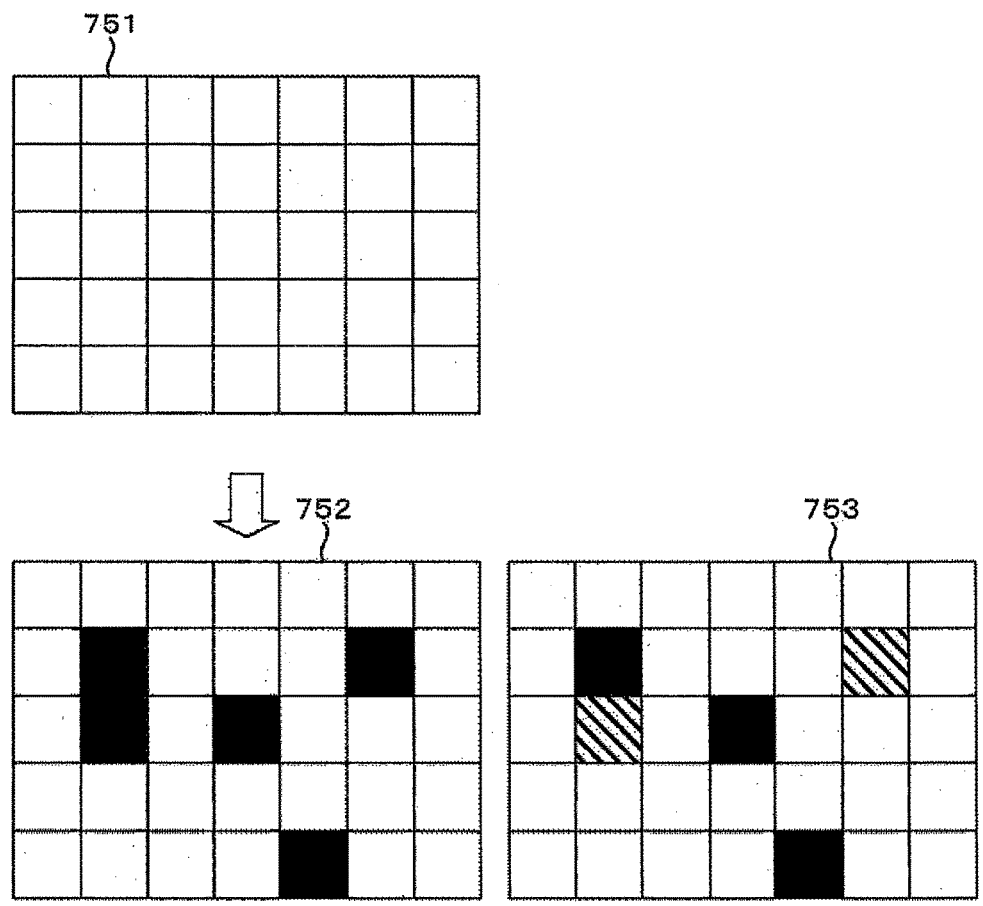

IMMUNOANALYSIS METHOD AND IMMUNOANALYSIS DEVICE

TECHNICAL FIELD

The present invention relates to an immunoanalysis method for measuring a substance to be measured in a sample and an immunoanalysis apparatus using the method.

BACKGROUND ART

Recently, as a method for analyzing a component to be measured which is contained in a sample, a method for easily analyzing the kind and the amount of the component to be measured has been developed. For example, a method which has been put to practical use is a method for analyzing a specific biological molecule by a so-called sandwich assay (enzyme-linked immunosorbent assay: ELISA), in which when the component to be measured is an antigen, a capture component (an antibody) which specifically binds to the antigen is immobilized on a support base material and is reacted with a sample to be measured to conduct a certain specific binding reaction, a labeled antibody is further reacted and the label is detected.

In examples of conventional analysis methods typified by ELISA (enzyme-linked immunosorbent assay), a capture component immobilized at a reaction site and a component to be measured are reacted and a fluorescently labeled secondary capture component is specifically reacted. The concentration of the component to be measured is calculated by measuring the fluorescence intensity of the labeled capture component bound to the reaction site.

CITATION LIST

Non Patent Literature
NPL 1: Science, Vol. 270, pp. 467-470, 1995
NPL 2: Proc. Natl. Acad. Sci., Vol. 103, pp. 3687-3692, 2006
NPL 3: Nature Biotechnology, Vol. 28, pp. 595-599, 2010

SUMMARY OF INVENTION

Technical Problem

Recently, there has been an increasing need for analyzing a component which exists in a sample in a trace amount, as typified by infectious diseases, tumor markers and the like. In a so-called low-concentration region where a trace amount of a component to be measured is contained in a sample, the fluorescence intensity derived from the desired reaction is often at a level close to that of the background of the fluorescent measurement. In such a low-concentration region, the signal derived from the reaction cannot be distinguished from the background signal of the measurement and this prevents the measurement with high sensitivity from being realized.

A single-molecule ELISA method which aims at the measurement with high sensitivity is disclosed in NPL 3. In this method, antibodies are immobilized on a microparticle and only one antigen in a diluted sample is bound to the antibody on the microparticle. The microparticle is collected/immobilized in a hole in a support and the component to be measured (the antigen) is then analyzed by measuring the label on the support.

However, because two or more antibodies are immobilized on the microparticle, the possibility that two or more antigens bind to one microparticle cannot be avoided. Because it is difficult to distinguish this state in a detection step, it is not possible to further improve the resolution of the antigen detection. In addition, it is said to be impossible to distinguish it in the detection step even when there is a hole on the support which is not occupied by the microparticle. This suggests that it is not possible to distinguish by the detection whether the antigen exists in the position or it corresponds to the background of the measurement without any antigen.

In view of the above problems, an object of the invention is to provide an analysis method and means which achieve the analysis with high sensitivity even in an extremely low-concentration region, in the analysis of a component to be measured which is contained in a sample.

Solution to Problem

The invention relates to an analysis method and an analysis apparatus which are constituted in such a way that a component to be measured and a capture component specifically reacting with the component to be measured are reacted and the reactant is labeled when the component to be measured is present and which are characterized by analyzing the component to be measured with single-molecule sensitivity and resolution by placing the labeled reactant in a spatially separated position and detecting the label of the labeled reactant.

In order to achieve the ultimate measurement with high sensitivity, a desirable constitution is that each labeled reactant molecule is placed in a spatially separated certain position, that is, each capture component molecule is placed in the detection position. However, in some cases, the constitution may not be essential for measuring the component to be measured. In a low-concentration region, there are not so many molecules of the component to be measured. Thus, even when two or more capture component molecules are placed in the detection position, it can be said that the possibility that two or more labeled reactant molecules are present in the detection position is not high and there is no serious hindrance in practical use in some cases.

In order to detect the labeled reactant, a constitution in which the labeled reactant molecules are placed in spatially separated certain positions is appropriate. Preferably, a constitution in which the labeled reactant molecules are arranged with spatial regularity, for example the molecules are arranged in a two-dimensional matrix, or the like is appropriate.

The label is preferably capable of optical labeling, such as fluorescent and luminescent labeling. It is possible to use a microparticle as the label and use the optical labeling derived from the particle, or parameters of physical properties such as the size of the microparticle may be used for labeling. Fluorescent pigments and the like may be used. That is, it is appropriate when it is possible to determine whether the component to be measured is present in the detection position or not and distinguish the presence of the component from the background of the measurement or the noise components, by detecting the label.

Various impurity components contained in the sample and the unreacted fluorescently labeled capture component prevent the precise measurement. It is thus preferable to remove them from the reaction system in advance. For this purpose, when a magnetic particle is used as the microparticle, a washing operation is easy and a practical, simple measurement system can be provided.

The component to be measured may be a component which is originally contained in a biological body, such as a protein or a hormone, or the component may be a virus, a drug or the like. When the component to be measured is an antigen, the capture component which specifically reacts is an antibody. On the contrary, when the component to be measured is an antibody, the capture component that specifically reacts is an antigen.

In a first example, the component to be measured is an antigen and an antibody which is the capture component specifically reacting with the antigen is placed in a spatially separated certain position on a support. The antigen, which is the component to be measured, reacts with the primary antibody in the certain position on the support. At the same time, the antigen to be measured also reacts with a labeled secondary antibody. From this, by placing each molecule of the labeled reactant in the spatially separated position on the support and detecting the label of the labeled reactant in the certain position, it is possible to analyze the component to be measured with single-molecule sensitivity and resolution.

As a second example, it is possible to immobilize an antibody which is the capture component specifically reacting with the antigen on a carrier such as a microparticle and in the end place the labeled reactant containing the microparticle in a spatially separated certain position on a support. That is, the primary antibody is immobilized on the carrier such as a microparticle and is reacted with the antigen, which is the component to be measured. Further, a labeled secondary antibody is reacted with the reactant containing the microparticle. By placing each labeled reactant molecule containing the microparticle in a spatially separated position on the support and detecting the label of the labeled reactant, the component to be measured can be analyzed with single-molecule sensitivity and resolution. The second example can be constituted in such a way that the reactions up to the generation of the labeled reactant progress in a solution. Thus, compared with the first example, the second example is preferable because high reaction efficiency can be expected. The diameter of the microparticle is preferably micrometer or nanometer order. The microparticle is not necessarily a magnetic particle but a magnetic particle is easy to handle.

In a third example, the labeled reactant is not placed on the support, but the labeled reactant is introduced to a flow path and each labeled reactant molecule is spatially separated and detected. That is, a primary antibody is immobilized on a carrier such as a microparticle and reacted with an antigen which is the component to be measured. Then, the reactant is reacted with a labeled secondary antibody. By introducing the labeled reactant in the flow path, spatially separating the labeled reactant molecules and placing each labeled reactant molecule in a detection position, the component to be measured can be analyzed with single-molecule sensitivity and resolution. The diameter of the microparticle is preferably micrometer or nanometer order. The microparticle is not necessarily a magnetic particle but a magnetic particle is easy to handle.

As a fourth example, an antigen as the component to be measured may be directly placed in a certain position of a support. However, the reaction efficiency in this case is not supposed to be high and thus this case is not practical as a routine analysis.

In the reaction processes of the above examples, when the labeled reactant is generated, the antigen, the primary antibody and the labeled secondary antibody as the reaction elements may be reacted in order to generate the labeled reactant, or some of the elements may be reacted in advance and another element may be then reacted. Alternatively, all the elements may be reacted at the same time.

Furthermore, in the above examples, steps for generating the labeled reactant have been described based on a so-called sandwich method as a process of the immunoanalysis method. However, the applications of the invention are not limited to the sandwich method and the invention can be applied for example to a competition method. In case when the component to be measured is analyzed by the competition method, the reaction elements are often an antigen, an antibody and a labeled antigen. In this case, the antigen and the labeled antigen compete when reacting with the antibody. In all the first example to the fourth example above, even when the competition method is used, as in the case of using the sandwich method, the component to be measured can be analyzed with single-molecule sensitivity and resolution by placing the labeled reactant molecule in a spatially separated position and detecting the label of the labeled reactant.

For the detection, each labeled reactant molecule, which is placed in the spatially separated state, may be counted. When one labeled reactant molecule is detected, it means that one molecule of the component to be measured is present. Thus, to count each labeled reactant molecule means to count the absolute molecule number of the component to be measured, and thus it is expected that a remarkably highly sensitive analysis is achieved. In many of the conventional analysis methods, the concentration of the component to be measured is measured instead of the absolute number of the molecules of the component to be measured. Although the measurement of the concentration is inferior to the measurement of the absolute number in terms of the measurement sensitivity, the environmental equipment for the measurement is simple. It is needless to say that the analysis method of the present proposal can be applied not only to the measurement of the absolute number but also the measurement of the concentration.

Advantageous Effects of Invention

According to the invention, it is possible to achieve a highly sensitive immunoanalysis with single-molecule sensitivity and resolution.

In addition, it is possible to analyze two or more components to be measured at the same time. Capture molecules which specifically react with the respective components to be measured are prepared and subjected to the reaction as described above, and thus two or more kinds of labeled reactant may be generated.

For the detection, by placing the labeled reactants in a spatially separated state and counting each molecule of the labeled reactants, the components to be measured can be analyzed at the same time with high sensitivity. It is possible to analyze using different kinds of label substance for the respective components to be measured, or a label substance can be used in common by sectioning the immobilization positions on the support by the component to be measured.

BRIEF DESCRIPTION OF DRAWINGS

FIG. 1 is a diagram for explaining an example of the analysis method of the Examples.

FIG. 2 is a diagram showing an example of the device constitution used for the analysis method of the Examples.

FIG. 3 is a diagram showing an example of the method for producing the device used for the analysis method of the Examples.

FIG. 4 is a diagram showing an example of the method for producing the single-molecule-immobilizing microparticle of the Examples.

FIG. 5A is a diagram showing an example of the analysis method of the Examples.

FIG. 5B is a diagram showing an example of the analysis method of the Examples.

FIG. 6 is a diagram showing an example of the analysis method of the Examples.

FIG. 7 is a diagram showing an example of the analysis apparatus for nucleic acids of the Examples.

DESCRIPTION OF EMBODIMENTS

Some Examples for carrying out the invention are explained below.

Example 1

The device constitution and the analysis method of this Example are explained using FIG. 1.

As shown in FIG. 1(a), in the device constitution of this Example, adhering pads 102 are formed on a support base material 101 and a microparticle 103 is immobilized on an adhering pad 102. On the microparticle 103, a capture molecule 104 is immobilized through a binding molecule 105.

As the support base material 101, a glass base plate such as quartz, a silicon wafer and the like can be used. The adhering pad 102 is made from a material which is different from the support base material 101 and a metal or a metal oxide can be used. The adhering pads 102 are preferably formed on the support base material 101 with regularity.

One microparticle 103 is immobilized on one adhering pad 102. Only one capture molecule 104 is immobilized on the microparticle 103 through the binding molecule 105.

Depending on the kind of component to be measured 106, molecule groups of various combinations can be used for the capture molecule 104 and the binding molecule 105. Alternatively, a molecule having avidin at the terminal may be used as the capture molecule 104. An alkane molecule having about 10 or less carbon atoms can be used as the binding molecule 105 and a molecule which binds to the capture molecule 104 through chemical bond and has biotin at the other terminal can be also used. In this case, it is desirable that the surface of the microparticle 103 is modified with avidin, streptavidin or the like.

An operator brings a sample containing the component to be measured 106 into contact with the device above. In this regard, in general, the sample also contains impurity components. The component to be measured 106 is captured by the capture molecule 104. The capture molecule 104 and the component to be measured 106 are bound to each other easily by general immunoreaction. As a result, the molecules of the component to be measured 106 are immobilized individually on the support base material 101 in a regular arrangement.

Next, as shown in FIG. 1(b), in order to count the number of the present immobilized molecules of the component to be measured 106, a reagent containing a fluorescently labeled capture molecule 108 is brought into contact with the base plate on which the component to be measured 106 is immobilized.

For fluorescent labeling, general fluorescent pigment molecules such as Cy3 and Cy5 and semiconductor microparticles made from Zn—Se or the like can be used. When the number of the components to be measured 106 which are to be identified is large, fluorescent beads containing a fluorescent substance can be used for fluorescent labeling. For example, when contents of two kinds of fluorescent substance are each classified into ten levels and the two kinds of fluorescent substance are mixed with different content levels, 100 kinds of fluorescent bead can be produced. When the number of fluorescent substance kinds is increased to three, a bead set capable of distinguishing 1000 kinds can be easily produced. For example, a fluorescent bead set capable of distinguishing 100 kinds by exciting with laser lights of two wavelengths is sold by Luminex Trading, Inc. By chemically modifying the surface of such a fluorescent bead and binding to the capture molecule, the fluorescently labeled capture molecule 108 can be produced.

After immobilizing the component to be measured 106 and the fluorescently labeled capture molecule 108 on the support base material by immunoreaction as described above, a non-specifically adsorbed substance and a free fluorescently labeled capture molecule 108 are removed from the reaction system by washing the device and fluorescent detection is then conducted (FIG. 1(c)). From this, the component to be measured 106 is analyzed.

In case of the fluorescently labeled capture molecule 108 having only one general fluorescent pigment molecule such as Cy3 or Cy5 as the fluorescent label, single-molecule fluorescence is observed from the part on the base plate to which the component to be measured 106 is immobilized. In this case, the fluorescence is weak and thus a fluorescence detector with high sensitivity such as EM-CCD is necessary.

When a fluorescent bead is used as the fluorescent substance, fluorescence stronger than the single-molecule fluorescence is emitted and thus satisfactory detection is possible also with general CCD.

The adhering pads 102 are formed on the support base material 101 with high regularity, for example in a lattice arrangement, and thus bright points of fluorescence are observed in positions with regularity also in a fluorescence image. Accordingly, also when the fluorescently labeled capture molecule 108 is non-specifically adhered to the support base material 101, by measuring the fluorescence in the positions of the bright points on the fluorescence image, the fluorescence signal derived from the desired reaction of the component to be measured can be easily distinguished from the fluorescence signal derived from the non-specific adsorption to the support or a noise of the fluorescent measurement. This point is a very useful characteristic in practical use, in the analysis of a trace amount of a sample or the observation of weak fluorescence.

With respect to the identification of the fluorescent substance or the fluorescent bead, the kind of fluorescent substance or fluorescent bead can be identified by separating the emission spectra using a diffraction grating, applying on the light-sensitive surface of CCD and measuring the intensity of each pixel divided in the wavelength direction. Alternatively, using a dichroic mirror whose reflection characteristic is highly dependent on the wavelength, the kind of fluorescent substance or fluorescent bead can be identified from the ratio of the reflected light and the transmitted light.

By identifying each bright point and then summarizing the results, the kind of component to be measured 106 and the number of the bright points, namely the information on the presence amount can be finally obtained. For example, when the adhering pads 102 are produced with a pitch of 1 μm, there are $10^6$ adhering pads in 1 mm square and it is thus possible to determine how many molecules of a certain kind of component to be measured exist among the maximum total molecule number of $10^6$.

Example 2

The device constitution of this Example is explained using FIG. 2.

Adhering pads 202 are formed on a support base material 201 regularly, for example in a lattice arrangement as shown in FIG. 2. The adhering pad 202 and a microparticle 203 are connected by chemical bond or chemical interaction through a linear molecule 205. A functional group 206 at the terminal of the linear molecule 205 and the adhering pad 202 are preferably bound to each other by chemical interaction. In this case, it is preferable that the interaction between the functional group 206 and the support base material 201 is weak and the interaction between the functional group 206 and the adhering pad 202 is strong.

From such viewpoints, as the support base material 201, quartz glass, sapphire, a silicon base plate and the like can be used.

In addition, the adhering pad 202 can be made from a material selected from gold, titanium, nickel and aluminum.

Although the functional group 206 should be selected considering the combination of the support base material 201 and the adhering pad 202, a sulfohydryl group, an amino group, a carboxyl group, a phosphate group, an aldehyde group and the like can be used for example.

The linear molecule 205 plays the role of connecting the microparticle 203 and the adhering pad 202. The length thereof is not particularly limited but a straight molecule of a length corresponding to about 3 to 20 carbon atoms is preferable when the linear molecule 205 is a low-molecular molecule.

A functional group 207 at the terminal of the linear molecule 205 achieves the adherence to the microparticle 203. In addition, when a high-molecular molecule is used as the linear molecule 205, a molecule which has two or more side chains and has both a side chain having the functional group 206 and a side chain having the functional group 207 can be used.

As the microparticle 203, a metal microparticle and a semiconductor microparticle can be used. For example, particles having diameters of 5 nm to 100 nm are commercially available as gold microparticles and can be used.

Furthermore, as the semiconductor microparticle, compound semiconductors having diameters of about 10 nm to 20 nm such as CdSe are commercially available and can be used.

The functional groups which can be used as the functional group 207 vary depending on the kind of microparticle, but a sulfohydryl group, an amino group and the like are preferable when a gold microparticle is used for example. When a semiconductor microparticle is used, a microparticle with a surface modified with streptavidin is commercially available and biotin can be used as the functional group 207.

In addition, it is also possible to use a microparticle made from a high-molecular material such as polystyrene as the microparticle 203. In case of a high-molecular material, the particle diameter of the microparticle can be made uniform and the particle diameter can be selected from a wide range from several dozen nm to several μm. Moreover, by modifying the surface using the functional group of the high-molecular material as a scaffold, the amount of the introduced functional group for the immobilization reaction of a capture molecule 204 which is immobilized on the microparticle surface can be made uniform, which is preferable. In particular, when only one capture molecule 204 is immobilized on the microparticle surface, the reproducibility of the immobilization rate is quite high, which is preferable.

For the capture molecule 204, an antibody which specifically reacts with the component to be measured can be used. The terminal of the antibody is modified in advance as in the functional group 207 and reacted with the microparticle 203. It is preferable that one capture molecule 204 is immobilized on one microparticle 203, and this means that only one capture molecule 204 is immobilized on the adhering pad 202.

When labeled capture molecules are identified by simple fluorescent detection, it is preferable that the labeled capture molecules are apart with a distance of about 1 μm, considering the limit of analysis. Accordingly, the appropriate size of the microparticle 203 is 1 μm or less.

As the method for forming the adhering pads 202 on the support base material 201, a thin-film process which has already been put into practice in the case of semiconductors can be used. For example, the adhering pads 202 can be produced by vapor deposition/sputtering through a mask, or by forming a thin film by vapor deposition/sputtering and then conducting dry or wet etching. The regular arrangement can be easily achieved by using the thin-film process. The distance between the pads can be arbitrarily set but the distance is preferably 1 μm or more considering the limit of diffraction of the light detection, when light measurement is conducted as the detection means.

After forming the adhering pads 202 on the support base material 201, the linear molecules 205, which connect the microparticles 203 and the adhering pads 202, are supplied and the linear molecules 205 are immobilized on the adhering pads 202. Here, for the purpose of preventing the non-specific adsorption on the support base material 201, a method in which a material which adheres strongly to the support base material 201 is reacted with the support base material 201 before supplying the linear molecules 205 is effective. For example, a silane coupling agent and the like can be used. Next, by supplying the microparticles 203 with the immobilized capture molecules 204 on the base plate and immobilizing the microparticles 203 on the adhering pads 202, a device for immunoanalysis is completed.

In this regard, it is possible to make the capture molecules capture the substance to be measured by supplying a device in which the capture molecules have already been immobilized as the device for immunoanalysis and bringing the measurement sample into contact with the device. Moreover, as another method, it is possible to bring a sample solution containing the substance to be measured into contact with a device, after supplying a device in which the adhering pads are regularly arranged on the support base material and immobilizing the microparticles to be immobilized on the adhering pads and the capture molecules specifically capturing the substance to be measured on the device.

When the microparticle 203 is immobilized on the adhering pad 202, two or more microparticles 203 may be immobilized on one adhering pad 202. When two or more microparticles 203 are immobilized, pieces of information on different kinds of component to be measured overlap and precise analysis becomes impossible. Accordingly, one microparticle 203 should be immobilized on one adhering pad 202.

Thus, the present inventors have repeated immobilization tests with various conditions and have concentrated on the investigation, and as a result the inventors have found that when the condition that the diameter d of the adhering pad 202 is smaller than the diameter D of the microparticle 203 is satisfied, one microparticle 203 can be immobilized on one adhering pad 202. The findings are explained by that when the microparticle 203 with a size which is the same as or larger than that of the adhering pad 202 is immobilized, the unreacted linear molecule is covered with the immobilized microparticle and cannot react with another microparticle.

As a result of further extensive investigation, it was found that when the surface of the microparticle 203 is charged, due to the electrostatic repulsion working between the microparticles, the number of the microparticle immobilized on one adhering pad is one even when the diameter d of the adhering pad 202 is larger than the diameter D of the microparticle 203.

Accordingly, it was elucidated that the diameter d of the adhering pad 202 is preferably smaller than the diameter D of the microparticle 203 when the surface of the microparticle 203 is weakly charged and the electrostatic repulsion is weak, while the diameter d of the adhering pad 202 is not necessarily smaller than the diameter D of the microparticle 203 when the surface of the microparticle 203 is strongly charged and the electrostatic repulsion is strong.

The publication of U.S. Pat. No. 6,859,570 discloses a method in which a hole (a small well) is provided at a terminal end of each optical fiber of an optical fiber bundle, a microparticle to which an antibody has been attached to capture the molecule to be measured is placed in the hole and the fluorescence is detected in each hole by the optical fiber. In the invention, such holes (small wells) are not necessary even when the microparticles are arranged in a lattice, and distribution of the microparticles in the holes rather causes problems such as prolonged time for thorough washing. Accordingly, in the invention, a method in which the microparticles are arranged in a lattice and immobilized on the support base material using the adhering pads is preferable, as described in this Example.

Example 3

In this Example, an example of the method for producing the microparticle having one immobilized capture molecule, in particular the method for immobilizing one capture molecule on one microparticle, is explained using FIG. 3.

On the surface of a microparticle 401, a binding site 402 for capturing a capture molecule 404 is bound. For example, streptavidin can be used as the binding site and a commercially available streptavidin-coated microparticle (Invitrogen, Inc.) can be used as the microparticle. The capture molecule 404 is modified with a binding site 403 in advance.

As the binding site 403, a binding site which easily binds to the binding site 402 on the surface of the microparticle 401 is selected. For example, when streptavidin described above is used as the binding site 402 for example, biotin is used as the binding site 403.

Next, the capture molecule 404 is bound to the microparticle 401 by reacting the microparticle 401 with the capture molecule 404.

In order to immobilize one capture molecule 404 on one microparticle 401, it is preferable to make the number of the capture molecules 404 in a unit volume smaller than the number of the microparticles 401. This is because the number of the capture molecules relative to one microparticle 401 is highly likely to be larger than one when the number of the capture molecules 404 is excessive as compared to the microparticles 401. According to the results of the investigation by the inventors, when the reaction was conducted with the number of the microparticles 401 10 times larger than the number of the capture molecules 404, about 90% of the microparticles 401 did not capture the capture molecules 404 and about 9% of the microparticles 401 each captured one capture molecule 404. This result corresponds well to the predicted result with the assumption of the Poisson distribution.

When only the microparticles 401 which have captured the capture molecules 404 as described above are collected, 90% or more of the collected microparticles 401 are microparticles 401 which have each captured one capture molecule 404. As the collection method, for example a method in which the capture molecule 404 is bound to a magnetic microparticle 407 and the composite of the magnetic microparticle and the microparticle is collected with a magnet is mentioned.

In this case, a molecule 405 which specifically reacts with the capture molecule 404 and is modified with a binding site 406 at the terminal is prepared and the surface of the magnetic microparticle 407 is coated with a binding site 408 which binds to the binding site 406 in advance. By mixing a thus produced reagent containing the magnetic microparticle 407 to the microparticle bound to the capture molecule, the magnetic microparticle 407 can be attached to the microparticle 401. By this method, the microparticles 401 which have each captured one capture molecule 404 can be separated and collected at a high ratio of 90% or more.

In order to isolate the collected microparticles 401 from the magnetic microparticles 407, for example, a high-temperature treatment can be used.

Thus, the isolated microparticles 401 are completed as a reagent for immunoanalysis in which one capture molecule 404 is immobilized on one microparticle 401.

Example 4

The analysis method of this Example is explained using FIG. 4 by an example in which the biological molecule to be analyzed is a protein.

A capture molecule (antibody) 1202 which is a capture component specifically binding to a component to be measured 1204 is immobilized on the surface of a magnetic microparticle 1201 through a binding molecule 1203. Although there is no specific restriction, the magnetic microparticle 1201 preferably has high dispersibility in order that the magnetic microparticle 1201 can react with the component to be measured efficiently in a solution. The diameter is preferably 100 micron or less, more preferably 10 micron or less.

By reacting the microparticle having the antibody with a sample containing the component to be measured, the component to be measured 1204 is captured on the magnetic microparticle 1201.

Next, by reacting a reagent containing a fluorescently labeled capture molecule 1205 having a fluorescent pigment label 1207 and an antibody as the capture component, the component to be measured 1204 captured by the magnetic microparticle 1201 is fluorescently labeled to generate a fluorescently labeled reactant.

Various impurity components contained in the sample and the unreacted fluorescently labeled capture component prevent the measurement and thus should be removed from the reaction system before the measurement. For this purpose, a washing operation is easy when the microparticle is a magnetic particle. That is, using a magnet, the magnetic microparticle 1201 is collected/immobilized on the surface of a support base material 1206 and the impurity components and the unreacted fluorescently labeled capture component 1205 which are not bound to the magnetic microparticle 1201 can be excluded from the reaction system by the washing operation.

Next, by applying a light to the surface of the support base material 1206, fluorescent bright points are counted by a detector. Because the number of the fluorescent bright points correlates with the molecule number of the component to be measured 1204, information on the molecule number of the component to be measured 1204 or the concentration thereof can be obtained by obtaining the number of the bright points. In particular, by preparing a reagent in which one antibody 1202 is immobilized on each magnetic microparticle 1201 in advance and using the reagent, the component to be measured 1204 can be analyzed with ultra-high sensitivity.

Example 5

Another measurement method of the invention is explained using FIG. 5A and FIG. 5B.

An antibody 1502 which is a capture component specifically binding to a component to be measured 1504 is immobilized on the surface of a microparticle 1501. Although there is no specific restriction, the microparticle 1501 preferably has high dispersibility in order that the microparticle 1501 can react with the component to be measured efficiently in a solution. The diameter is preferably 100 micron or less, more preferably 10 micron or less. By reacting the microparticle having the antibody with the component to be measured in a solution, the component to be measured 1504 is captured on the microparticle 1501.

Next, by reacting an antibody 1505 which is a capture component having a fluorescent pigment label 1507, the component to be measured 1504 captured by the microparticle 1501 can be fluorescently labeled and a fluorescently labeled reactant can be generated. As the fluorescent label, a fluorescent pigment and a fluorescent bead containing a fluorescent substance can be used.

Then, the fluorescently labeled reactant 1508 is introduced to a flow path 1509 shown in FIG. 5B and the fluorescence from the fluorescently labeled reactant is measured with a detector 1510 by applying an excitation light. By adjusting the diameter of the flow path 1509 to two times or less as large as the diameter of the microparticle 1501, the fluorescence of each fluorescently labeled reactant particle can be measured without measuring the fluorescence of two or more fluorescently labeled reactant particles at the same time, which is preferable.

Example 6

In this Example, an example of a preferable constitution of the immunoanalysis apparatus using the device for immunoanalysis is explained referring to FIG. 6.

The immunoanalysis device in this Example has a constitution in which the fluorescently labeled capture molecules can be arranged in a matrix, namely a structure in which the adhering pads are arranged in a matrix.

The analysis apparatus of this Example has means for supplying a sample solution to be measured, a capture reagent containing magnetic particles, a fluorescently labeled capture reagent and a washing solution, temperature-controlling means for conducting immunoreaction, means for washing the magnetic microparticles, means for washing a device for immunoanalysis, means for applying a light to a device base plate for immunoanalysis, and luminescence-detecting means for measuring the luminescence derived from the fluorescently labeled capture reagent.

More specifically, the sample solution to be measured and the capture reagent containing the magnetic particles are dispensed into a reaction container and reacted, and the fluorescently labeled capture reagent is then added and the reaction is further progressed. The temperature of the reaction container is kept at 37° C. After a certain period of time, a magnet is placed around the reaction container and a reaction product containing the magnetic particles is collected. By repeating an operation of discharging the reaction solution from the reaction container and then adding the washing solution, the reactant containing the magnetic particles is washed. By this washing operation, the impurity components derived from the sample and the free fluorescently labeled capture reagent are excluded from the reaction system.

A solution-sending unit 705 is connected to an inlet 714 and the sample solution to be measured, the capture reagent containing the magnetic particles, the fluorescently labeled capture reagent and the washing solution are supplied from the solution-sending unit 705. The reaction solution in which the reaction product containing the magnetic particles has been generated by the reaction with the magnetic particles is dispersed again and then sent to the device for immunoanalysis. By a magnet unit 716 acting on the reaction solution, the magnetic particles are collected and immobilized in adhering pads arranged in a matrix on an analysis device base plate 701.

Next, fluorescence is detected. An appropriate excitation light source can be selected depending on the kind of fluorescent substance used. For example, when Cy5, Cy5.5 and Cy3 are used as the fluorescent substances used for the fluorescent beads, two kinds of excitation light of 532 nm (YAG laser) and 633 nm (He—Ne laser) are appropriate. Laser lights emitted from a YAG laser light source (wavelength of 532 nm, output of 20 mW) 707 and a He—Ne laser light source (wavelength of 633 nm, output of 20 mW) 713 are adjusted by a dichroic mirror 715 in such a way that that the two laser lights have the same axis and then the laser lights are led to an object lens 706 by a dichroic mirror 709 and applied on the analysis device base plate 701 for immunization.

The fluorescence emitted from the fluorescently labeled molecule by applying the excitation light travels in a light path having the same axis as the excitation light but in the reverse direction and is collected by the object lens 706. Then, the fluorescence passes the dichroic mirror 709 and forms an image on a photosensitive surface of a two-dimensional CCD camera 712 by an image-forming lens 711. The scattered excitation light is removed by an optical filter 710.

After the analysis is finished, by removing the effect of the magnet unit 716 to fix the magnet particles, the sample solution flows through a flow path 704 and is discharged to an outlet 716. Thus, the magnet unit 716 is desirably disposed movably relative to the analysis device base plate 701. Then, the analysis device base plate 701 for immunization is washed by the means for washing the device for immunoanalysis.

Examples of the measurement results obtained by the immunoanalysis apparatus of this Example are shown in FIG. 7.

An image 751 of a two-dimensional CCD camera in which fluorescence of an unreacted immunoanalysis device was measured, and measurement results 752 and 753 which are images of a CCD camera in which fluorescence measured from analysis devices for immunization after the reaction was measured with a YAG laser and a He—Ne laser are shown.

The measurement result 752 is a result of the measurement of PSA (a prostatic cancer marker) in a sample, and the measurement result 752 indicates that the fluorescently labeled capture molecules were detected, that is, the PSA molecules in the sample were detected, in positions which are indicated with a dark color in the diagram for the convenience. In this case, when the CCD camera 712 obtains an image from the analysis device, the CCD camera 712 counts the number of bright points appearing in the lattice matrix and calculates the concentration of PSA in the measurement sample based on the number of the bright points.

Similarly, the measurement result 753 is a result of the simultaneous measurement of PSA and AFP (a liver cancer marker) in a sample. The diagram shows that the fluorescently labeled capture molecules derived from PSA were detected in positions which are indicated with a dark color for the convenience and the fluorescently labeled capture molecules derived from AFP were detected in shaded positions. Because a capture antibody capable of capturing two or more markers was attached on each adhering pad in the lattice matrix, the two components, namely PSA and AFP, in the same sample could be detected by single treatment and this means that the PSA molecules and the AFP molecules in the sample can be detected at the same time.

In this case, when the CCD camera 712 obtains an image from the analysis device, the CCD camera 712 counts the numbers of bright points appearing in the lattice matrix in an image 752 and calculates the concentrations of PSA and AFP contained in the sample based on the numbers of the bright points.

In this regard, although an analysis device in which the fluorescently labeled capture molecules are arranged in a lattice matrix is used in this Example, for example, a constitution in which the fluorescently labeled capture molecules are aligned in a line or arranged on a circle is also acceptable. In short, it is desirable that the arrangement has any regularity and undetected positions and detected positions can be distinguished.

REFERENCE SIGNS LIST

101: Support Base Material
102: Adhering Pad
103, 1501: Microparticle
104, 1202: Capture Molecule
106: Component To Be Measured
108, 1205, 1305: Fluorescently Labeled Capture Molecule
511, 610: Detector
701: Analysis Device Base Plate
702: Material Forming Flow Path
704, 1509: Flow Path
705: Solution-Sending Unit
706: Object Lens
707: YAG Laser Light Source
708: Lens
709, 715: Dichroic Mirror
710: Optical Filter
711: Image-Forming Lens
712: CCD Camera
713: He—Ne Laser Light Source
1201: Magnetic Microparticle

The invention claimed is:

1. An immunoanalysis device, comprising:
two or more immobilizing means which are disposed on a flat surface of a support base material in a spatially separated state;
supplying means for supplying a reactant generated by reacting a sample solution containing a substance to be measured with a plurality of magnetic microparticles which are bound with the substance to be measured by a first antigen-antibody reaction, and further supplying a fluorescently labeled capture reagent containing a plurality of fluorescently labeled capture molecules which are configured to further bind with the substance to be measured by a second antigen-antibody reaction;
a magnet which is movable relative to the support base material to collect and bind the magnetic microparticles to the immobilizing means; and
measuring means to measure signal information from the fluorescently labeled capture molecules which are bound to the substance to be measured,
wherein only one of the magnetic microparticles is bound to each one of the immobilizing means,
wherein only one particle of the substance to be measured is immobilized on each one of the magnetic microparticles bound to the immobilizing means, and
wherein the measuring means is configured to obtain the signal information and position information of the substance which is bound to the magnetic microparticles bound to the immobilizing means by counting a number of bright spots corresponding to the substance which is bound to the magnetic microparticles bound to the immobilizing means.

2. The immunoanalysis device of claim 1, wherein the two or more immobilizing means are disposed on the support base material in a matrix.

3. The immunoanalysis device of claim 1,
wherein the surface of the support base material that the two or more immobilizing means are disposed on is one of quartz glass, sapphire and a silicon base plate, and
wherein the two or more immobilizing means are constituted by one of gold, titanium, nickel, and aluminum disposed on the support base material.

4. The immunoanalysis device of claim 1,
wherein a distance between adjacent ones of the immobilizing means is at least 1 μm.

5. The immunoanalysis device of claim 1,
wherein a diameter of the magnetic microparticles is 1 μm or more.

6. The immunoanalysis apparatus of claim 1,
wherein the measuring means is an image-measuring means for measuring a luminescence signal from the fluorescently labeled capture molecules as an image.

7. The immunoanalysis device of claim 1,
wherein a diameter of each one of the immobilizing means is less than a diameter of each one of the magnetic microparticles.

8. An immunoanalysis device, comprising:
a support base material;
a plurality of adhering pads disposed on the support base material in a spatially separated state;
supplying means for supplying a reactant generated by reacting a sample solution containing a substance to be measured with a plurality of magnetic microparticles which are bound with the substance to be measured by a first antigen-antibody reaction, and further supplying a fluorescently labeled capture reagent containing a plurality of fluorescently labeled capture molecules which are configured to further bind with the substance to be measured by a second antigen-antibody reaction;
a magnet which is movable relative to the support base material to collect and bind the magnetic microparticles to the immobilizing means; and
one or more light sources and a two-dimensional detector to measure signal information from the fluorescently labeled capture molecules which are bound to the substance to be measured,
wherein a plurality of linear molecules are bound to each of the adhering pads,
wherein only one of the magnetic microparticles is bound to each one of the immobilizing means by the linear molecules,
wherein only one particle of the substance to be measured is immobilized on each one of the magnetic microparticles bound to the immobilizing means, and
wherein the two-dimensional detector is configured to obtain the signal information and position information of the substance which is bound to the magnetic microparticles bound to the immobilizing means by counting a number of bright spots corresponding to the substance which is bound to the magnetic microparticles bound to the immobilizing means.

9. The immunoanalysis device of claim 8, wherein the adhering pads are disposed on the support base material in a matrix.

10. The immunoanalysis device of claim 8,
wherein a surface of the support base material is one of a quartz glass, a sapphire and a silicon base plate, and
wherein the adhering pads are constituted by one of gold, titanium, nickel, and aluminum disposed on the support base material.

11. The immunoanalysis device of claim 8,
wherein a distance between adjacent adhering pads is at least 1 μm.

12. The immunoanalysis device of claim 8,
wherein a diameter of each of the magnetic microparticles is 1 μm or more.

13. The immunoanalysis device of claim 8,
wherein a diameter of each of the magnetic microparticles is greater than a diameter of each of the adhering pads.

14. A method for producing an immunoanalysis device, comprising the steps of:
forming two or more immobilizing means on a support base material;
supplying a reactant generated by reacting a sample solution containing a substance to be measured with a plurality of magnetic microparticles which are bound with the substance to be measured by a first antigen-antibody reaction, and further supplying a fluorescently labeled capture reagent containing a plurality of fluorescently labeled capture molecules which are configured to further bind with the substance to be measured by a second antigen-antibody reaction;
moving a magnet relative to the support base material to collect and bind the magnetic microparticles to the immobilizing means; and
measuring signal information from the fluorescently labeled capture molecules which are bound to the substance to be measured,
wherein only one of the magnetic microparticles is bound to each one of the immobilizing means,
wherein only one particle of the substance to be measured is immobilized on each one of the magnetic microparticles bound to the immobilizing means, and
wherein the measuring obtains the signal information and position information of the substance which is bound to the magnetic microparticles bound to the immobilizing means by counting a number of bright spots corresponding to the substance which is bound to the magnetic microparticles bound to the immobilizing means.

* * * * *